Feb. 23, 1965 R. S. MOORE Plant Pat. 2,484
MINIATURE ROSE PLANT
Filed Nov. 5, 1963
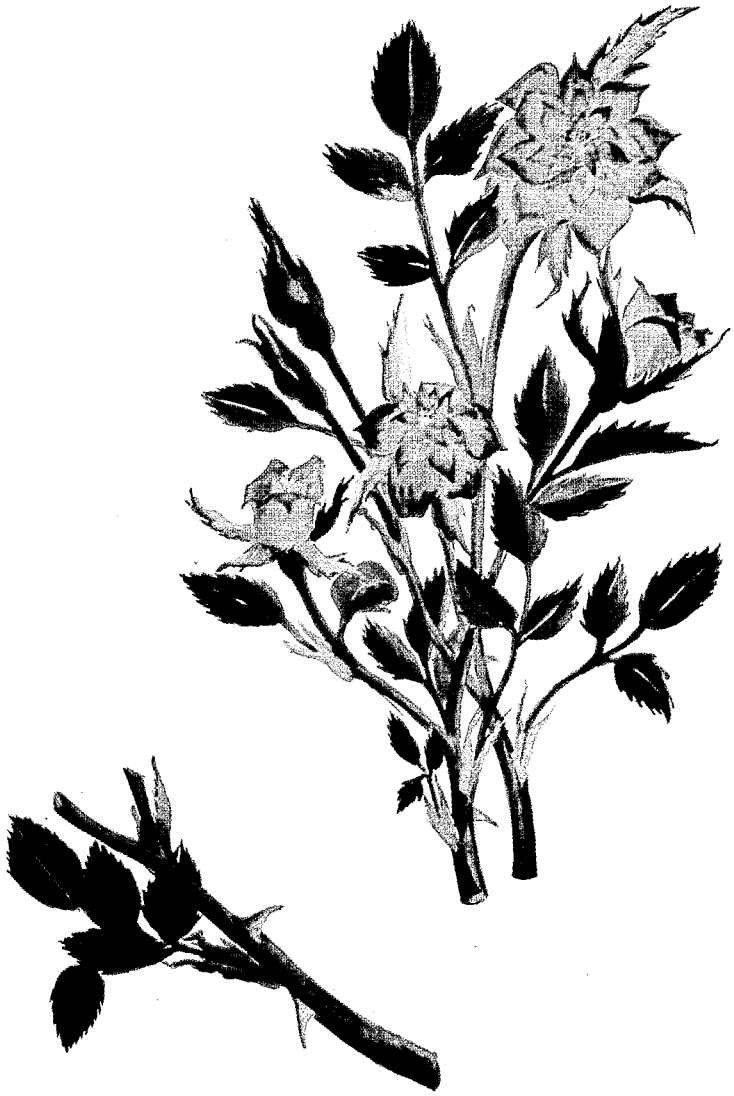
WITNESS
Jeanette Nunn Copley
INVENTOR
Ralph S. Moore United States Patent Office Plant Pat. 2,484
Patented Feb. 23, 1965

2,484
MINIATURE ROSE PLANT

Ralph S. Moore, 2519 E. Mineral King, Visalia, Calif.

Filed Nov. 5, 1963, Ser. No. 321,708
1 Claim. (Cl. Plt.—10)

The present invention relates to a new and distinct variety of hardy, dwarf, bush type rose plant of the hybrid miniature class; the variety being primarily characterized—as to novelty—by double velvety red flowers which are similar to the Dian miniature rose (Plant Patent 1,808), except that the color is deeper red.

The variety is further characterized by:

An abundance of bloom, with flowers borne singly or several to the stem in loose clusters.

A plant which is vigorous, of rounded upright habit, and with semi-glossy, dark green, medium-small foliage. The plant, which has a normal average height of 12" to 16" at maturity, resembles the general plant habit of the Dian miniature rose.

A plant which grows and blooms satisfactorily both in the greenhouse and outdoors; is a good potted plant; and provides excellent garden decoration as well as cut flowers.

The present variety of miniature rose was originated by me in my nursery located at Visalia, California, under conditions of careful control and observation, as a cross between an unnamed and unpatented seedling (*Rosa wichuraiana* × Floradora, both unpatented) as the seed parent, and another unnamed and unpatented seedling (Oakington Ruby × Floradora, both unpatented) as the pollen parent.

Subsequent to origination of the variety I successfully asexually reproduced it, in my nursery located as aforesaid, by budding as well as by cuttings; the reproductions having run true in all respects.

The figure of the drawing illustrates a spray, including foliage, buds and flowers.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy; dwarf; bush; seedling; greenhouse; outdoors; cut flowers; garden decoration; potted plant.

Class: Hybrid miniature.

Flowers:

*Continuity.*—Continuous.

*Fragrance.*—Slight, apple.

Flowers borne: Usually singly, on 3" to 4" stem, or several together in loose cluster; sturdy wiry stems.

Quantity of bloom: Average abundance both outside and in greenhouse.

Bud:

*Peduncle.*—Medium length; slender; erect; medium green, often tinted bronze; numerous reddish thorns.

*Before calyx breaks.*—Size—small. Form long; pointed; usually with foliaceous appendages on surface of the bud; with foliaceous parts extending beyond the tip of the bud equal to one-half or more of its length. Color—dark green, sometimes tinted bronze.

*As calyx breaks.*—Color—red.

*As first petal opens.*—Size—small. Form—long; pointed. Color: outside—Indian Lake 826—pale yellow-green at base; inside—Ruby Red 827—shading to lighter red near base thence into near-white and pale yellow-green at base.

*Opening.*—Usually opens well.

Bloom:

*Size when fully open.*—Small, averaging 1½". Petalage.—Very double—45 to 50 petals, arranged regularly.

*Form.*—High centered and full at first, with petals rolled loosely outward, and later at maturity being loosely rolled outward.

Petals: Fairly thick; leathery; velvety inside; satiny outside.

*Shape.*—Outside petals broad lanceolate; intermediate—broad lanceolate; inside—lanceolate.

*Color.*—Newly opened flower from a plant grown outdoors (October 1963), Visalia, California. Outside petal: outside surface—Indian Lake 826/3, with dilution of white near base; near-white to pale yellow-green at base; inside surface—Indian Lake 826, shading into near-white at base. Intermediate petal: outside surface—Indian Lake 826/3, shading into near-white at base; inside surface—Indian Lake 826 shading into near white with a bit of pale yellow-green at base. Inner petal: outside surface—Indian Lake 826/3 or lighter, shading into near-white at base; inside surface—Indian Lake 826/1, shading into near-white on lower half of petal.

*General color effect.*—Newly opened flower—dark red. Three days open—dark red.

*Behaviour.*—Petals usually drop clean. Petal color often darkens as flower ages, showing blackish shadings.

*Flower longevity (October 1963).*—Bush in garden—4 to 7 days. Cut flowers kept at living room temperature—3 to 5 days.

Reproductive organs:

*Stamens.*—Very few to none; arranged irregularly. Mixed with petaloids if present.

*Filaments.*—Short; white.

*Anthers.*—Small; yellow.

*Pollen.*—Very scarce.

*Pistils.*—Moderate number.

*Styles.*—Uneven; medium length, bunched.

*Stigma.*—White.

*Ovaries.*—All enclosed in calyx.

*Hips.*—None.

*Sepals.*—Permanent; spear shaped; nearly flat, sometimes slightly recurved.

*Seeds.*—None.

Foliage:

*Leaves.*—Compound of five leaflets; abundant; moderately leathery; semi-glossy.

*Leaflets.*—Shape—lanceloate; apex acute; base round (sometimes pointed). Margin—serrate. Color—dark green; new growth sometimes tinted bronze. Rachis—medium strength; upper surface grooved with a few small thorns or prickles; under side sparsely thorny. Stipules—medium length; fairly broad; short length points, turning out at an angle of more than 45 degrees.

Growth:

*Habit.*—Dwarf; bushy; upright; much branched.

*Growth.*—Free; vigorous.

*Canes.*—Medium.

*Main stems.*—Color—dull green. Thorns—moderately thorny; long oval base; medium length; hooked downward; color—brown or reddish brown. Prickles—none. Hairs—none.

*Branches.*—Color—medium green. Thorns—moderately thorny; medium length; hooked downward; long oval base; color—red-brown.

*New shoots.*—Color—bright green, often tinted bronze. Thorns—moderately thorny; medium length; hooked downward; long oval base; color—reddish. Prickles—none. Hairs—none.

The miniature rose plant and its flowers as herein described may vary in slight detail due to climatic, soil and cultural conditions under which the variety may be grown; the present description being of the variety as grown at Visalia, California.

The following is claimed:

A new and distinct variety of miniature rose plant of hardy, dwarf, upright, much branched, bush type, as illustrated and described, characterized by buds and flowers resembling the Dian miniature rose in general form but with a more high centered flower and longer, more pointed buds; the flowers being a dark red color of velvety texture; the overall effect of bush and flower being that of the Dian miniature rose except that the foliage is more abundant, not so glossy, and the flower is a darker red color; and further characterized by a plant which is vigorous in growth, easy to propagate from cuttings, with medium-small semi-glossy dark green foliage, an abundance of bloom, with flowers borne singly or several to stem in loose clusters.

No references cited.

ABRAHAM G. STONE, *Primary Examiner.*